US008501202B2

(12) United States Patent
Stiefel

(10) Patent No.: US 8,501,202 B2
(45) Date of Patent: *Aug. 6, 2013

(54) SULFACETAMIDE FORMULATIONS FOR TREATMENT OF SKIN DERMATOSES

(75) Inventor: Charles W. Stiefel, Miami, FL (US)

(73) Assignee: Aqua Pharmaceuticals, LLC, West Chester, PA (US)

( * ) Notice: Subject to any disclaimer, the term of this patent is extended or adjusted under 35 U.S.C. 154(b) by 1356 days.

This patent is subject to a terminal disclaimer.

(21) Appl. No.: 11/340,073

(22) Filed: Jan. 26, 2006

(65) Prior Publication Data

US 2006/0239944 A1    Oct. 26, 2006

Related U.S. Application Data

(63) Continuation-in-part of application No. 10/937,741, filed on Sep. 10, 2004, now Pat. No. 7,357,938, which is a continuation-in-part of application No. 10/191,880, filed on Jul. 9, 2002, now Pat. No. 7,022,332.

(60) Provisional application No. 60/304,019, filed on Jul. 9, 2001.

(51) Int. Cl.
*A61K 8/02* (2006.01)

(52) U.S. Cl.
USPC ............... 424/401; 424/59; 424/60; 424/400; 424/703; 514/859; 514/861; 514/863; 514/864

(58) Field of Classification Search
USPC .............. 424/401, 59, 60, 400, 703; 514/859, 514/861, 863, 864
See application file for complete search history.

(56) References Cited

U.S. PATENT DOCUMENTS

| | | | |
|---|---|---|---|
| 4,847,071 A | | 7/1989 | Bissett et al. |
| 4,888,327 A | * | 12/1989 | Edwards ........................ 514/41 |
| 4,895,727 A | | 1/1990 | Allen |
| 5,017,366 A | | 5/1991 | Stiefel et al. |
| 5,567,420 A | | 10/1996 | McEleney et al. |
| 6,211,250 B1 | * | 4/2001 | Tomlinson et al. ........ 514/772.4 |
| 6,482,839 B1 | | 11/2002 | Thornfeldt |
| 6,514,489 B1 | | 2/2003 | Shacknai et al. |
| 7,022,332 B2 | * | 4/2006 | Stiefel ........................... 424/401 |
| 2003/0118526 A1 | | 6/2003 | Stiefel |
| 2005/0089485 A1 | * | 4/2005 | Stiefel ............................. 424/59 |

FOREIGN PATENT DOCUMENTS

| | | |
|---|---|---|
| CA | 2161737 A1 | 5/1997 |
| EP | 0692254 | 7/1994 |
| WO | 03/006005 A1 | 1/2003 |

OTHER PUBLICATIONS

E. Bonner, et al., The Demodex mite population in rosacea, Journal of the American Academy of Dermatology, Mar. 1993, pp. 443-448.
Jonathan K. Wilkin, Flushing Disorders, Principles and Practice of Dermatology, Sams and Lynch Editors, 1990, pp. 495-500.
Food and Drug Adminstration, Sunscreen Drug Products for Over-The-Counter Human Use, Final Monograph, Federal Register, May 21, 1999, vol. 64, No. 98, pp. 1-54.
British Pharmacopoeia 1999, vol. I, pp. 1353-1354.
Draelos, "Cosmetics", http://www.emedicine.com/derm/topic502.htm, printed Aug. 8, 2006.
Cosmetic Ingredient Dictionary, "Search Results For: Silica", http://www.cosmeticcop.com/learn/dictionary.asp?keys=silica&pos=1&type=FIND, printed Aug. 8, 2006.
21 C.F.R. § 352.10 (Apr. 1, 2006 edition), "Subpart B—Active Ingredients", http://www.access.gpo.gov/nara/cfr/waisidx_06/21cfr352_06.html, printed Aug. 8, 2006.
21 C.F.R. § 352.76 (Apr. 1, 2006), "Determination if a product is water resistant or etc.," http://www.access.gpo.gov/nara/cfr/waisidx_06/21cfr352_06.html, printed Aug. 8, 2006.
Bradley Pharmaceuticals, Inc., "Sulfacet R labeling", http://www.bradpharm.com/intl/dermik.html, printed Aug. 10, 2006.
Bradley Pharmaceuticals, Inc., "Sulfacet R labeling", http://www.bradpharm.com/intl/pdf/SULF2-Ins.pdfhtml, printed Aug. 10, 2006.
Lebwohl, et al., "The Comparative Efficacy of Sodium Sulfacetamide 10%/Sulfur 5% (Sulfacet-R®) Lotion and Metronidazole 0.75% (MetroGel®) in the Treatment of Rosacea", J. of Geriatric Dermatology, vol. 210, pp. 500-512, (2004).
Buechner, "Rosacea: An Update", Dermatology, vol. 210, pp. 100-108, (2005).
Pelle, et al., "Continuing Medical Education: Rosacea: II. Therapy", J. Am. Acad. Dermatol., vol. 51, No. 4, pp. 500-512, (2004).
Wells, et al., Cosmetics and the Skin. New York: Reinhold Publishing Corp., 1964.
Rieger, (Ed.). Harry's Cosmeticology (8th Ed.), New York, NY, Chemical Publishing Co., 2000.
Lebwohl, et al., "The Comparative Efficacy of Sodium Sulfacetamide 10%/Sulfur 5% (Sulfacet-R®) Lotion and Metronidazole 0.75% (MetroGel®) in the Treatment of Rosacea", J. of Geriatric Dermatology, vol. 3, No. 5, pp. 183-185, (1995).
Draelos, "Sunscreens", Cosmetics in Dermatology, Churchill Livingston Inc., pp. 164-166, (1990).
Nichols, et al., "Effective Sunscreen Ingredients and Cutaneous Irritation in Patients with Rosacea", Cutis, vol. 61, pp. 344-346, (1998).
"Sunscreen Drug products for Over-the-Counter Human Use; Amendment to the Tentative Final Monograph, Enforcement Policy", 63 Fed. Reg. 56584 (Oct. 22, 1998).
The United States Pharmacopeia, Twentieth Revision, Official from Jul. 1, 1980, United States Pharmacopeial Convention, Inc., p. 744.
Physicians' Desk Reference, Sulfacet R® lotion Edition 31, pp. 755-756, (1977).
Sauder, et al., "The treatment of rosacea: the safety and efficacy of sodium sulfacetamide 10% and sulfur 5% lotion (Novacet) is demonstrated in a double-blind study", J. Derm. Treat, vol. 8, pp. 79-85, (1997).

* cited by examiner

*Primary Examiner* — Fereydoun G Sajjadi
*Assistant Examiner* — Danielle Sullivan
(74) *Attorney, Agent, or Firm* — Leydig, Voit & Mayer, Ltd.

(57) ABSTRACT

A topical composition for the treatment of mammalian skin dermatoses comprising a sulfacetamide or a derivative thereof and at least 1 sunscreen wherein the sunscreen is present in a sufficient amount to produce a sun protection factor of about 1.6 to about 20.6. Also provided is a method of treating mammalian dermatoses by administering a topical composition comprising a sulfacetamide or a derivative thereof and at least 1 sunscreen wherein the sunscreen is present in a sufficient amount to produce a sun protection factor of about 1.6 to about 20.6.

21 Claims, No Drawings

SULFACETAMIDE FORMULATIONS FOR TREATMENT OF SKIN DERMATOSES

CLAIM OF PRIORITY

This application is a continuation-in-part of U.S. patent application of Ser. No. 10/937,741, filed Sep. 10, 2004, now U.S. Pat. No. 7,357,938 which is a continuation-in-part of U.S. patent application Ser. No. 10/191,880, filed Jul. 9, 2002, now U.S. Pat. No. 7,022,332 which claims priority to U.S. Provisional Application Ser. No. 60/304,019 filed on Jul. 9, 2001, the contents of which are hereby expressly incorporated by reference in their entirety.

TECHNICAL FIELD

This invention relates to sulfacetamide formulations for the treatment of skin dermatoses.

BACKGROUND OF THE INVENTION

Dermatoses is a disease of the skin. One form of dermatoses is rosacea. Rosacea is an acne form condition primarily affecting the areas of the nose, cheeks, and forehead of adults. The condition is characterized by erythema, papules, rhinophyma, and telagiectases. The cause of rosacea is unknown, however, dietary influence, gastrointestinal disturbances, psychologic or hormonal imbalance, sebaceous gland abnormalities, and infection have been considered but not validated. Other theories range from solar-induced dermal connective tissue damage, with resultant vascular distension to humorally mediated active vasodilatory changes. A causative role has also been suggested for the hair follicle mite, Demodex, C. E. Bonnard, et al., *The Demodex Mite Population*, J. Amer. Acad. Dermatology, Vol. 28, No. 3, pp. 443-447, March 1993.

Dermatoses or other skin disorders refers generally to any condition, infection, disease or disorder which afflicts the skin of a patient. Sodium sulfacetamide with and without sulfur has been utilized for many years to treat acne. A nominal treatment concentration for sodium sulfacetamide is 10% and for sulfur is 5%. Sulfacet R® by Dermik Laboratories is a marketed example of such products.

Sulfur alone has been used to treat skin diseases, such as acne, for over 100 years. Sulfur products have been used at levels up to 10% to treat acne. Sulfur has also been combined with resorcinol to improve its performance.

The use of UV absorbers to counteract the sensitizing effects of some dermatological therapeutics has been described in the art. For example, the use of UV absorbers in combination with erythromycin for the treatment of acne is described in U.S. Pat. No. 5,017,366.

A. P. Kelly (Principles and Practice of Dermatology, Sams and Lynch editors, 1990, p. 789) indicates that avoidance of sun exposure is a mechanism to be explored in the management of the skin flushing often seen with rosacea. J. K. Wilkins stated (Id, p. 495) that "the degree to which reddening occurs results not only from the intensity of the flushing reaction, but also from the pigmentation of the subject and the visibility of the vessels, which may be enhanced in a sun-damaged dystrophic dermis."

Many skin disorders are treated with a single course of therapy on the premise that the etiology and presented symptoms are the result of a single cause. Unfortunately, many diseases, especially skin diseases, are complicated in that the symptoms may be the result of changes in internal, external, or a combination of both environments. As a result, conventional single agent therapies have been shown not to yield the desired clinical results demonstrated, for example, as cosmetic improvement (appearance), elimination of pathogenic organisms, reduction of swelling, etc. Skin disorders where two or more conditions have been identified include acne and rosacea.

Antibacterial compositions for dermatological treatment must remain stable for long periods of time (useful shelf life), not lose its potency (a known characteristic of antibiotics under certain conditions), not form insoluble substances or complexes because of the combining sulfacetamide and other active ingredients, and also not be especially irritating to the skin.

Sunscreens are designed to protect against sunburn caused by UVB rays and generally provide little protection against UVA rays. UVA rays are linked to aging and generally have a depressing effect on the immune system and therefore may lead to other dermatological problems such as rosacea.

Missing in the art is a convenient means to ensure patient compliance with topical administration of a sulfacetamide and a sunscreen. At present, there is no commercially available product containing both a sulfacetamide and a sunscreen.

There has also been great difficulty in the art in preparing a topical composition that can effectively be administered for treating skin dermatoses that contains both sulfacetamide and a sunscreen. Such compositions for dermatological treatment of skin dermatoses must remain stable for long periods of time, not lose their potency, not form insoluble substances or complexes because of the combining sulfacetamide and other active ingredients, and must minimize irritation to the skin. There is a lack of such compositions in the art for treatment of skin dermatoses.

Accordingly, there remains a need in the art for a stable topical composition having effectiveness in treating skin dermatoses than the presently known compositions.

SUMMARY OF THE INVENTION

The present invention is directed towards a topical composition for the treatment of mammalian skin dermatoses comprising a sulfacetamide or a derivative thereof and at least 1 sunscreen wherein the sunscreen is present in a sufficient amount to produce a sun protection factor of about 1.6 to about 20.6. This invention is also directed toward a method of treating mammalian dermatoses by administering a topical composition comprising a sulfacetamide or a derivative thereof and at least 1 sunscreen wherein the sunscreen is present in a sufficient amount to produce a sun protection factor of about 1.6 to about 20.6.

This invention is also directed towards a topical composition for the treatment of mammalian skin dermatoses comprising sulfacetamide and at least one sunscreen, wherein the sunscreen is present in a sufficient amount to produce a sun protection factor of about 1.6 to about 20.6 and wherein the composition is chemically stable for more than 180 days at 25° C. This invention is also directed towards a topical composition for the treatment of mammalian skin dermatoses comprising sulfacetamide and at least one sunscreen wherein the sunscreen is present in a sufficient amount to produce a sun protection factor of about 1.6 to about 20.6 and wherein the composition exhibits less than 10% decomposition of sulfacetamide or sunscreen after storage at 25° C. for 180 days.

DETAILED DESCRIPTION OF THE INVENTION

The present invention comprises a sulfacetamide and a sunscreen in combination for the treatment of skin dermatoses. This combination product is directed to the multifaceted etiology of rosacea and other skin dermatoses. The novel combination of sodium sulfacetamide and a sunscreen described herein offers the clinician a regimen which would be an effective treatment of this often unsightly skin condition.

The compositions described herein are useful in the treatment of bacterial disorders of the skin. In a preferred embodiment, the present compositions involve the treatment of bacterial disorders that exhibit effects such as skin lesions, inflammation, swelling, redness, pustules, cysts, nodules, papules, hypertrophy of the sebaceous glands, combinations thereof and a variety of other skin effects.

The present compositions involves treatment of bacterial disorders that may be selected from the group consisting of topical bacterial infections, impetigo, folliculitis, erythrasma, bacterial vaginosis, and combinations thereof. The bacterial disorder may be gram positive bacteria, gram negative bacteria and combinations thereof. Non-limiting examples of gram positive bacteria treatable herein include *Streptococcus* sp., *Micrococcus* sp., *Staphylococcus* sp., *Bacillus* sp., *Corynebacterium* sp., *Clostridium* sp. and combinations thereof. Non-limiting examples of treatable particular bacterial infections include *S. viridans, S. agalactiae, S. pyogenes, S. faecalis, S. durans, S. faecium, S. mutans, S. sanguis, S. salivarius, S. mitior, S. constellatus, S. intermedius, S. anginosus, S. milleri, S. iniae, S. pneumoniae, S. aureus, S. epidermis, C. minutissimum, C. jeikeium, C. urealyticum, C. xerosis, C. perfringens, C. tetani, C. botulinum, C. difficile, Escherichia coli, Pasteurella multocida, Aeromonas hydrophila, Vibrio vulnificus, P. aeruginosa, Pseudofolliculitis barbae, Pyoderma gangrenosum, Listeria monocytogenes* and combinations thereof.

The compositions disclosed herein are capable of treating a wide variety of skin disorders, including other skin conditions, infections, diseases, or disorders associated with, related to or commonly further occurring in skin affected by bacterial disorders. Such other skin disorders include antimicrobial resistant bacterial infections, atopic dermatitis, bromhidrosis, chronic paronychia, desquamative inflammatory vaginitis, Fox Fordyce Disease, Hailey-Hailey Disease, Hidradenitits suppurativa, intertrigo, nummular dermatitis, otopyorrhea, perioral dermatitis, angular chelitis, psoriasis, seborrheic dermatitis, skin ulcers, and combinations thereof.

The topical drug delivery system used to formulate the present invention may be either aqueous, hydro-alcoholic, or non-aqueous in composition and may include polymers, liposomes, surfactants, thickeners, or other pharmaceutically acceptable ingredients which would enhance the product's acceptance. Such formulations are generally known in the art.

A preferred topical delivery system is emulsion based. However, other topical pharmaceutical dosage forms, such as suspensions, should also be operative. The active ingredients may be dissolved, dispersed, suspended, solubilized, coated, entrapped, or encapsulated within the formulation matrix by a variety of techniques known in the art.

Acceptable levels of sodium sulfacetamide are from 1 to 20%, more preferably 5 to 15%, and most preferably 9 to 11.5%. Acceptable levels of sulfur are from 1 to 20%, more preferably from 2.5 to 10%, and most preferably from 4.5 to 5.5%. While the preferred sulfacetamide is sodium sulfacetamide, other salts and derivatives which function in the treatment of mammalian skin dermatoses would also be suitable.

A variety of UV absorbers are known in the art and have varying effectiveness at absorbing different parts of the UV spectrum. A preferred embodiment of the present invention would include a UV absorber component that has activity in both the UVA and UVB ranges. This may be accomplished either through the use of a UV absorber that is effective in both the UVA and the UVB ranges or through the use of two or more UV absorbers having combined activity across the UVA and UVB spectra. The most preferred embodiment of the topical composition includes a combination of the UV absorbers avobenzone and octylmethoxycinnamate.

UV absorbers encompassed by this invention include, but are not limited to, the use of one or more of the following: benzophenone derivatives (such as benzophenone-1, benzophenone-2 or benzophenone-3 [also known as oxybenzone], benzophenone-4, benzophenone-6, benzophenone-8, benzophenone-12, dioxybenzone, cinoxate, ensulizole, sulisobenzone, bismidazylate, camphor benzalkonium methosulfate, diethylamino hydroxybenzoyl hexyl benzoate, diethylexyl butamide triazone, dimethicodiethylbenzal malonate, drometrizole trisiloxane, ecamsule, ensulizole, octyl triazone, polyacrylamideomethyl benzylidene camphor, tinosorb M, tinosorb S, alkyl and aryl cinnamate derivatives (such as DEA methoxycinnamate, octyl methoxycinnamate, isoamyl p-methozycinnamate), aminobenzoate derivatives (such as p-aminobenzoic acid, ethyl dihydroxypropyl p-amino benzoic acid, glyceryl p-aminobenzoic acid, octyl dimethyl p-aminobenzoic acid, PEG-25 PABA), homosalate, anthranilate derivatives (such as menthyl anthranilate), aryl acrylate derivatives (such as etocrylene, octocrylene), salicylate derivatives (such as octyl salicylate, trolamine salicylate), benzimidazole derivatives (such as 2-phenylbenzimidazole-5 sulphonic acid), benzilidene derivatives (such as 3-(4-methylbenzylidene)-camphor, benzylidene camphor sulfonic acid), benzoyl methane derivatives (such as 4-isopropyl dibenzoyl methane, butyl methoxy dibenzoyl methane [also known as avobenzone]) and oxides (such as titanium dioxide and zinc oxide).

The amount of UV absorber employed will depend on its effectiveness, alone or in combination with other UV absorbers, but in any event will be sufficient to block a measurable quantity of UV radiation, preferably that UV radiation generated naturally, such as by the sun, or generated by man-made UV radiation generating sources, such as electric lamps and beams.

The UV absorbers or sunscreens are preferably mixed with benzyl alcohol as a solubilizer. Benzyl alcohol or benzenemthanol is a constituent of jasmine, hyacinth, ylang-ylang oils, Peru and Tolu balsams, and storax. The UV absorbers are solublized in benzyl alcohol to ensure a homogenous mixture with the other components of the composition. Benzyl alcohol is commonly present in topical compositions as a preservative, but is not commonly known as a solubilizing agent.

The most preferred UV absorbers and their concentration by weight is set forth in Table 1:

TABLE 1

UV Absorbers & Concentration

| UV Absorbers | % w/w |
| --- | --- |
| avobenzone | 0.1 to 5% |
| octocrylene | 0.1 to 15% |
| octyl methoxycinnamate | 0.1 to 10% |
| oxybenzone | 0.1 to 10% |

Compositions embodying the present invention are described in detail the examples that follow. Examples One and Two are most preferred. As set out below, the most preferred composition is a combination of UV absorbers and includes levels of avobenzone that are 2.7 to 3.3% in combination with octyl methoxycinnamate at 6.75 to 8.25%.

Example One

The ingredients of Example One are set forth in Table 2.

TABLE 2

Example One Ingredients (% W/W)

| | % W/W |
|---|---|
| Phase A Ingredients | |
| Purified Water | 49.29 |
| Edetate Disodium | 0.500 |
| Sodium Phosphate Monobasic (Dihydrate) | 0.0100 |
| Phase B Ingredients | |
| Cetostearyl Alcohol | 1.50 |
| Steareth-2 | 2.25 |
| Steareth-21 | 2.75 |
| Emulsifying Wax, NF | 4.00 |
| Octyl Methoxycinnamate | 7.50 |
| $C_{12-15}$ Alkyl Benzoate | 5.00 |
| Propylene Glycol | 5.50 |
| Avobenzone | 3.00 |
| Dimethicone | 0.500 |
| Sodium Sulfacetamide | 10.7 |
| Precipitated Sulfur | 5.00 |
| Phase C Ingredients | |
| Purified Water | 1.00 |

TABLE 2-continued

Example One Ingredients (% W/W)

| | % W/W |
|---|---|
| Benzyl Alcohol | 1.00 |
| Sodium Thiosulfate | 0.500 |
| To Make Total | 100.0 |

Directions for Preparation

Create Phase "A" by combining purified water, edetate disodium and sodium phosphate monobasic (dihydrate) in a suitable vessel. While mixing, heat to about 70° C. In a separate suitable container create Phase "B" by combining cetostearyl alcohol, steareth-2, steareth-21, emulsifying wax (NF), octyl methoxycinnamate, $C_{12-15}$ alkyl benzoate, propylene glycol, avobenzone and dimethicone. Heat to about 70° C. while mixing to make uniform. To Phase "B" add and disperse the sulfur and sodium sulfacetamide. Then add Phase "B" to Phase "A" while mixing and continue to mix for about 30 minutes. Cool resulting mixture (Phase "AB") to about 40° C. while continuously mixing. Then add the benzyl alcohol to Phase "AB" and continue cooling and mixing. Add the sodium thiosulfate pre-dissolved in the purified water. Mix until uniform.

Stability Testing

The composition of Example One was placed on stability at FT (Freeze-Thaw; a stability test where the composition is subject to alternating periods of freezing and warm environments), 6° C., 25° C., 30° C., and 40° C. All samples placed on stability were maintained at the constant temperature indicated. The freeze thaw samples were subjected to alternate periods of freezing (−10 to −20° C.) and warmer environments, such as room temperature (15-30° C.). This test is used to accelerate emulsion and solution instability in hopes of finding problems early in development. Each sample was observed weekly for the first 4 weeks and once a month for months two through six. Chemical analysis were completed on samples taken after storage at the designated temperatures for the stated number of days over a six month test period. The results of the chemical analysis are set forth in Table 3 below and the physical observations are set forth in Table 4 below.

TABLE 3

Example One Chemical Analysis

| Ingredient | #Days | Specification (% WAV) | FT | 6° C. | 25° C. | 30° C. | 40° C. |
|---|---|---|---|---|---|---|---|
| Sodium Sulfacetamide | 7 | 9-11 | | | 10.84 | | |
| Sodium Sulfacetamide | 96 | 9-11 | 10.68 | 10.87 | 10.54 | 10.40 | 10.36 |
| Sodium Sulfacetamide | 186 | 9-11 | | 10.94 | 10.70 | 10.61 | 10.06 |
| Sulfur | 7 | 4.5-5.0 | | | 4.75 | | |
| Sulfur | 96 | 4.5-5.0 | 4.88 | 4.79 | 5.10 | 4.91 | 5.04 |
| Sulfur | 186 | 4.5-5.0 | | 4.63 | 4.65 | 4.8.5 | 5.04 |
| Avobenzone | 7 | 2.7-3.30 | | | 3.00 | | |
| Avobenzone | 96 | 2.7-3.30 | 2.98 | 2.97 | 2.95 | 2.93 | 2.93 |
| Avobenzone | 186 | 2.7-3.30 | | 2.92 | 2.92 | 2.93 | 2.88 |
| Octyl Methoxycinnamate | 7 | 6.75-8.25 | | | 6.89 | | |
| Octyl Methoxycinnamate | 96 | 6.75-8.25 | 7.48 | 7.42 | 7.29 | 7.39 | 7.56 |
| Octyl Methoxycinnamate | 186 | 6.75-8.25 | | 7.48 | 7.44 | 7.44 | 7.50 |
| Benzyl Alcohol | 96 | 0.90-1.10 | 1.12 | 0.99 | 1.01 | 1.01 | 0.97 |
| Benzyl Alcohol | 186 | 0.90-1.10 | | 0.99 | 1.00 | 1.01 | 0.98 |
| pH | 96 | NA | 7.42 | 7.39 | 7.39 | 7.43 | 7.42 |
| pH | 186 | NA | | NA | 7.22 | NA | 7.25 |

TABLE 4

Example One Physical Appearance

| Day | Temperature | Appearance |
|---|---|---|
| 0 | 25° | A pale yellow smooth homogenous cream |
| 7 | All | Same as initial |
| 14 | All | Same as initial |
| 21 | All | Same as initial |
| 28 | All | Same as initial |
| 53 | 40° | Same as initial with slight aeration |
| 53 | All others | Same as initial |
| 95 | FT, 6°, 25° | Same as initial. |
| 95 | 30° | Same as initial with slight aeration |
| 95 | 40° | Product has darkened and become aerated. |
| 186 | All | Same as day 95 |

Example Two

Ingredients

The ingredients of Example 2 are set forth in Table 5.

TABLE 5

| Example Two Ingredients (% W/W) | |
|---|---|
| | % W/W |
| Phase A Ingredients | |
| Purified Water | 43.79 |
| Edetate Disodium | 0.500 |
| Sodium Phosphate Monobasic (Dihydrate) | 0.0100 |
| Phase B Ingredients | |
| Cetostearyl Alcohol | 1.50 |
| Steareth-2 | 2.25 |

TABLE 5-continued

| Example Two Ingredients (% W/W) | |
|---|---|
| | % W/W |
| Steareth-21 | 2.75 |
| Emulsifying Wax, NF | 4.00 |
| Oxybenzone | 6.00 |
| $C_{12-15}$ Alkyl Benzoate | 5.00 |
| Propylene Glycol | 5.50 |
| Octocrylene | 10.0 |
| Dimethicone | 0.500 |
| Sodium Sulfacetamide | 10.7 |
| Precipitated Sulfur | 5.00 |
| Phase C Ingredients | |
| Purified Water | 1.00 |
| Benzyl Alcohol | 1.00 |
| Sodium Thiosulfate | 0.500 |
| To Make Total | 100.0 |

Directions for Preparation

Create Phase "A" by combining purified water, edetate disodium and sodium phosphate monobasic (dihydrate) in a suitable vessel. While mixing, heat to about 70° C. In a separate suitable container create Phase "B" by combining cetostearyl alcohol, steareth-2, steareth-21, emulsifying wax (NF), oxybenzone, $C_{12-15}$ alkyl benzoate, propylene glycol, octocrylene and dimethicone. Heat to about 70° C. while mixing to make uniform. To Phase "B" add and disperse the sulfur and sodium sulfacetamide. Then add Phase "B" to Phase "A" while mixing and continue to mix for about 30 minutes. Cool resulting mixture (Phase "AB") to about 40° C. while continuously mixing. Then add the benzyl alcohol to Phase "AB" and continue cooling and mixing. Add the sodium thiosulfate pre-dissolved in the purified water. Mix until uniform.

The formulation of Example Two was stored in clear vials capped with black polyseal lined screw caps and tested for stability at 40, 30, 25, 6 and FT. The samples were observed and assayed at 7 days and 3 months.

Stability Testing

The composition of Example Two was placed on stability at FT, 6° C., 25° C., 30° C., and 40° C. Each sample was observed weekly for the first 4 weeks and once a month for months two through six. Chemical analysis were completed on samples taken after storage at the designated temperatures for the stated number of days over a six month test period. The results of the chemical analysis are set forth in Table 6 below and the physical observations are set forth in Table 7 below.

TABLE 6

| Example Two Chemical Analysis | | | | | | | |
|---|---|---|---|---|---|---|---|
| Ingredient | #Days | Specification {% % WAV) | FT | 6° C. | 25° C. | 30° C. | 40° C. |
| Sodium Sulfacetamide | 7 | 9-11 | | | 10.60 | | |
| Sodium Sulfacetamide | 96 | 9-11 | 10.67 | 10.61 | 10.68 | 10.34 | 10.19 |
| Sulfur | 7 | 4.5-5.0 | | | 4.63 | | |
| Sulfur | 96 | 4.5-5.0 | 4.97 | 4.92 | 5.12 | 5.45 | 5.36 |
| Octocrylene | 7 | 9.00-11.00 | | | 9.54 | | |
| Octocrylene | 96 | 9.00-11.00 | 9.60 | 9.61 | 9.64 | 8.89 | 9.37 |
| Oxybenzone | 7 | 5.4-6.6 | | | 5.86 | | |
| Oxybenzone | 96 | 5.4-6.6 | 5.99 | 5.97 | 5.99 | 5.51 | 5.84 |
| Benzyl Alcohol | 96 | 0.9-1.10 | .90 | .92 | .90 | .90 | .88 |
| PH | 96 | NA | 7.35 | 7.43 | 7.46 | 7.53 | 7.55 |

TABLE 7

| Example Two Physical Appearance | | |
|---|---|---|
| Day | Temperature | Appearance |
| 0 | 25° | A pale yellow smooth homogenous cream |
| 7 | 40° | Slight darkening of product, but otherwise as |
| 7 | All others | Same as initial |
| 14 | All | Same as day 7 |
| 21 | 30° | Slightly darker than day 7. |
| 21 | 40° | Same as day 7. |
| 21 | All others | Same as initial |
| 28 | All | Same as day 21 |
| 53 | 40° | Same as day 21 with slight aeration |
| 53 | All others | Same as day 28 |
| 95 | FT, 6°, 25° | As initial with very slight aeration |
| 95 | 30° | Product has darkened and become aerated |
| 95 | 40° | Product has become aerated. A brown layer has formed on the bottom ⅓ of the vial with the |
| 186 | 25° | Aeration more pronounced than at 95 days |
| 186 | All others | Same as day 95 |

Example Three

Ingredients

The ingredients of Example Three are set forth in Table 8

TABLE 8

Example Three Ingredients (% W/W)

| | % W/W |
|---|---|
| Phase A Ingredients | |
| Purified Water | 46.29 |
| Edetate Disodium | 0.500 |
| Sodium Phosphate Monobasic (Dihydrate) | 0.0100 |
| Phase B Ingredients | |
| Cetostearyl Alcohol | 2.00 |
| Steareth-2 | 2.00 |
| Steareth-21 | 3.00 |
| Emulsifying Wax, NF | 5.00 |
| Avobenzone | 1.00 |
| $C_{12-15}$ Alkyl Benzoate | 5.00 |
| Propylene Glycol | 4.00 |
| Octyl Methoxycinnamate | 5.00 |
| Dimethicone | 0.500 |
| Zinc Oxide Dispersion | 3.50 |
| Titanium Dioxide Dispersion | 4.00 |
| Sodium Sulfacetamide | 10.7 |
| Precipitated Sulfur | 5.00 |
| Phase C Ingredients | |
| Purified Water | 1.00 |
| Benzyl Alcohol | 1.00 |
| Sodium Thiosulfate | 0.500 |
| To Make Total | 100.0 |

Directions for Preparation

Create Phase "A" by combining purified water, edetate disodium and sodium phosphate monobasic (dihydrate) in a suitable vessel. While mixing, heat to about 70° C. In a separate suitable container create Phase "B" by combining cetostearyl alcohol, steareth-2, steareth-21, emulsifying wax (NF), C12-15 alkyl benzoate, propylene glycol, and dimethicone. Heat to about 70° C. while mixing to make uniform. To Phase "B" add and disperse the sulfur, sodium sulfacetamide, zinc oxide and titanium dioxide. Then add Phase "B" to Phase "A" while mixing and continue to mix for about 30 minutes. Cool resulting mixture (Phase "AB") to about 40° C. while continuously mixing. Then add the benzyl alcohol to Phase "AB" and continue cooling and mixing. Add the sodium thiosulfate pre-dissolved in the purified water. Mix until uniform.

Compositions as disclosed herein may be administered to a patient suffering from a skin disorder by thinly applying the composition topically to affected areas of the face 1-3 times per day.

SPF Testing (In Vitro)

Ten (10) compositions with varying sunscreen components were tested to determine their relative sunscreen protection factor using an in vitro procedure employing the Optometrics Corporation SPF290 instrument. The ten formulations were made according to the procedures set out in Examples One, Two and Three with the only variable being the sunscreen components. Data were generated using Transpore® surgical tape as a substrate. Test materials are applied to the tape and the UV light absorbance measured. Results generated are reported in Table 9. These measurements provide an assessment of potential product SPF the true value of which may only be established in a human clinical evaluation.

TABLE 9

SPF (In Vitro) Testing Results

| Formulation Components | SPF Value | +/−SD |
|---|---|---|
| Sodium Sulfacetamide 10% Sulfur 5% Avobenzone 3% Octyl Methoxycinnamate 7.5% Oxybenzone 6% | 14.9 | 3.0 |
| Sodium Sulfacetamide 10% Sulfur 5% Avobenzone 3% Octocrylene 10% Octyl Methoxycinnamate 7.5% | 12.1 | 2.6 |
| Sulfacetamide Sodium 10% Sulfur 5% Octocrylene 10% Octyl Methoxycinnamate 7.5% Oxybenzone 6% | 11.9 | 2.0 |
| Sodium Sulfacetamide 10% Sulfur 5% Octyl Methoxycinnamate 7.5% Octocrylene 10% Octyl Salicylate 5.0% | 8.3 | 1.2 |
| Sodium Sulfacetamide 10% Sulfur 5% Octyl Methoxycinnamate 7.5% Sulisobenzone 10% | 10.4 | 2.3 |
| Sodium Sulfacetamide 10% Sulfur 5% Octocrylene 10% Octyl Methoxycinnamate 7.5% | 8.3 | 0.7 |
| Sodium Sulfacetamide 10% Sulfur 5% Avobenzone 3% Octyl Methoxycinnamate 7.5% | 11.4 | 3.7 |
| Sodium Sulfacetamide 10% Sulfur 5% | 1.6 | 0.1 |
| Sodium Sulfacetamide 10% Sulfur 5% Octocrylene 10% Oxybenzone 6% | 12.2 | 2.9 |
| Sodium Sulfacetamide 10% Sulfur 5% Avobenzone 3% Octyl Methoxycinnamate 7.5% | 11.6 | 2.2 |

CONCLUSION

Data generated show that the addition of sunscreen agents increases the relative SPF values found when compared to the product without added sunscreens. Also shown is the effect of the combination of avobenzone and octylmethozycinnamate as being as effective, and in some instances, more effective than the combination of three UV absorbers. The use of two UV absorbers instead of three lowers the potential of sensitization or allergic reactions due to a fewer number of ingredients. The use of two UV absorbers instead of three also provides for a lower cost of manufacturing the composition.

SPF Testing (In Vivo)

Five of the above compositions were tested with a homosalate control to determine their relative sunscreen protection factor by following an FDA approved human clinical study design. Forty-six subjects (43 female, 3 male) with one of the following skin types and sunburn and tanning histories: I) Always burns easily; never tans (sensitive), II) always burns easily; tans minimally (sensitive), III) burns moderately; tans gradually (normal). Each subject's inherent MED (minimal erythema dose) was determined by exposing the unprotected skin on their backs to ultraviolet radiation in a series of doses is or timed intervals. Twenty-two to twenty four hours post exposure the series of doses were evaluated to determine the smallest dose of energy that produced redness reaching the borders of the exposure site (MED). This procedure was repeated concurrently with the test products for confirmation (MED Unprotected Control Site).

The subjects were sequentially placed into two groups. Group 1 tested the first two test articles (as listed in Table 10) and the 8% homosalate control and group 2 tested the second three test articles (as listed in Table 10) and the 8% homosalate control (applied to their backs) with the sequence of test articles predetermined by randomization. A series of seven ultraviolet radiation exposures were administered within each treatment area as outlined in the FDA Final Monograph.

Following exposure of the sub sites with ultraviolet radiation, a visual evaluation was conducted for the presence or absence of an immediate response (darkening, reddening or heat response) and noted. The sub sites were covered and evaluated 22-24 hours after exposure, in a blinded manner, to determine the MED. Reactions to the ultraviolet exposures were graded using a scale of 0-3+ is where 0=no reaction, ±=minimal erythema, the first perceptible, redness reaction with clearly defined borders, 1+=defined erythema, 2+=moderate erythema, and 3+=severe erythema. Results generated are reported in Table 10.

Calculation of SPF

For each subject, the SPF value for each test article sunscreen was calculated by dividing the dose of ultraviolet radiation (Joules/cm$^2$ required to produce the MED of the protected skin (MED Protected Skin) by the dose of ultraviolet radiation (joules/cm$^2$ required to produce the MED of the unprotected skin (MED Unprotected Control Site).

The label SPF value for each test article formulation was determined as follows: Calculate the mean SPF value (x). Determine the standard deviation(s). Obtain the upper 5% point from the t distribution table with n−1 degrees of freedom (t). Compute ts/<radical>n and denote by (A). The label SPF equals the largest whole number less than x−A. (See the FDA Final Monograph: FR May 21, 1999, Vol. 64, No. 98). It is recommended that the standard error be determined and not exceed five percent of the mean.

TABLE 10

SPF (In Vivo) Testing Results

| Formulation Description | SPF Value | ±SD | Label SPF |
|---|---|---|---|
| Sodium Sulfacetamide 10% | 20.6 | 2.6 | 19 |
| Sulfur 5% | | | |
| Avobenzone 3% | | | |
| Oxybenzone 6% | | | |
| Octyl Methoxycinnamate 7.5% | | | |
| Sodium Sulfacetamide 10% | 19.9 | 1.8 | 19 |
| Sulfur 5% | | | |
| Avobenzone 3% | | | |
| Octocrylene 10% | | | |
| Octyl Methoxycinnamate 7.5% | | | |
| Sodium Sulfacetamide 10% | 20.4 | 3.4 | 18 |
| Sulfur 5% | | | |
| Octocrylene 10% | | | |
| Octyl Methoxycinnamate 7.5% | | | |
| Oxybenzone 6% | | | |
| Sodium Sulfacetamide 10% | 20.1 | 3.2 | 18 |
| Sulfur 5% | | | |
| Octocrylene 10% | | | |
| Octyl Methoxycinnamate 7.5% | | | |
| Sodium Sulfacetamide 10% | 20.3 | 3.4 | 18 |
| Sulfur 5% | | | |
| Avobenzone 3% | | | |
| Octyl Methoxycinnamate 7.5% | | | |

Data generated show each of the compositions exhibit a sun protection factor.

Metronidazole Comparative Study

A clinical study was carried out to compare the efficacy and safety of the present compositions to a currently marketed rosacea treatment having metronidazole as the active ingredient. The study was a double-blind, parallel group study in which approximately 140 subjects (20-32 subjects/site for six sites) with rosacea were randomly assigned to twice daily treatment with either of two compositions for twelve weeks. The first composition comprised the composition of Example 1 comprising a 10% sodium sulfacetamide and 5% sulfur cream with sunscreens. The second composition comprised the commercially available MetroCream® composition comprising 0.75% metronidazole, available from Galderma International of La Defense Cedex, France.

Study subjects were required to be at least 16 years of age and to have clinical evidence of rosacea with a minimum of 10 and a maximum of 39 inflammatory lesions (papules and pustules) and at least moderate erythema. Subjects were not allowed to use medicated cleansers containing benzoyl peroxide, sodium sulfacetamide, or salicylic acid, or rosacea or acne treatments of any type including miticides, pediculocides, and corticosteroids, for defined periods of time before study entry and throughout the study. Subjects were excluded from study entry if they used cimetidine, lithium, disulfiram, coumarin, anticoagulants, niacin, frequently used vasodilators with known flushing activity, or any medication that would interfere with the study results. Subjects were to minimize the use of spicy foods, very hot foods and drinks, caffeinated and alcoholic beverages, and exposure to sunlight including sunlamps during the study.

Efficacy and safety were evaluated initially (week 0) and at all subsequent visits (weeks 3, 6, 9, and 12). Evaluation of efficacy was performed by counting total facial inflammatory lesions (papules and pustules) and grading facial erythema and global rosacea severity at all visits. Subject's assessment of global improvement relative to the subject's initial condition was also made at weeks 3, 6, 9 and 12.

Seventy-five subjects were entered to test the composition of Example 1, and 77 subjects were entered into the Metro-Cream® group for a total of 152 subjects. One hundred and thirty-eight subjects completed the study with ten dropouts in the Example 1 group and four dropouts in the MeroCream® group. The demographic and baseline features of the subjects were similar for both groups. The demographic population consisted primarily of female Caucasian adults.

Data analyses for efficacy were performed on all subjects who had data after baseline regardless of whether the protocol was followed (intent to treat subjects) with imputations made by carrying forward the last available observation. Statistaical methods included analyses of variance for lesion count data and the Cochran-Mantel-Haenszel procedure for categorical data. Effects considered were site and treatment.

The primary efficacy variable, symmetrized percent reduction from baseline of inflammatory lesion counts, with significantly greater for the composition of Example 1 than MetroCream® at week 12. The least square mean symmetrized percent reduction was back calculated to 80% reduction for the composition of Example 1 and 72% reduction for MetroCream®. There was no difference for the other primary efficacy variable, proportion of subjects with success for investigator global severity (reduction from baseline by at least 2 grades), at week 12 for the composition of Example 1 (78%) compared to the MetroCream® group (68%). For the second efficacy variables, the Example 1 group had a significantly greater proportion of subjects (69%) with improvement in erythema score (reduction by at least 1 grade) at week 12 than the MetroCream® group (45%) and success with subject global improvement (cleared, excellent or good) at week 12 was also significantly greater for the composition of Example 1 (79%) than for MetroCream® (59%).

TABLE 11

Comparison of Results at Week 12 for All Subjects

| Parameter | Example 1 formulation | MetroCream |
|---|---|---|
| Number of subjects enrolled | 75 | 77 |
| Mean age in years | 48 | 46 |
| Percent male/female | 28/72 | 29/71 |
| Investigator Global Severity | | |
| % of subjects with success at week 12 | 78 | 68 |
| p-value: comparison to MetroCream | 0.1894 | NA |
| Inflammatory Lesions | | |
| LS mean % reduction at week 12 | 80 | 72 |
| p-value: comparison to MetroCream using symmetrized % reduction | 0.0424 | NA |
| Erythema | | |
| % of subjects with improved erythema at week 12 | 69 | 45 |
| p-value: comparison to MetroCream | 0.0007 | NA |
| Subject Global Improvement | | |
| % of subjects with cleared, excellent or good at week 12 | 79 | 59 |
| p-value: comparison to MetroCream | 0.0131 | NA |
| Overall Tolerance (all subjects) | | |
| % of subjects with good or excellent | 88% | 100% |

* LS Mean = least square mean (from analysis of variance with effects for site and treatment)

Overall, this study suggests that twice daily use of the composition of Example 1 is an effective regimen for treatment of rosacea and is more effective than metronidazole treatments. In particular, the present compositions appear to be significantly more effective than currently available treatments, notably those having metronidazole as the sole active ingredient. In particular, the present compositions appear to be more effective than MetroCream, a specific metronidazole based treatment. Such metronidazole based treatments are presently considered by some to be the treatment of choice for rosacea. This result is unexpected given the previously studied treatments using sulfacetamide. The enhanced efficacy of the composition as demonstrated herein is believed to result from the present unique combination of a sulfacetamide or a derivative thereof and a sunscreen.

Accordingly, it would further be expected that the use of the composition of Example 1 is more effective than topical metronidazole treatments comprising about 0.5% to about 1.5% metronidazole in the treatment of rosacea. In particular, it would be expected that the present compositions are more effective than topical metronidazole treatments comprising about 0.75% or about 1% metronidazole in the treatment of rosacea.

Additionally, it would be expected that the results herein described would be similarly observed for any period of treatment or treatment regimen useful in treating rosacea. This includes daily administration of the compositions during the period of treatment, twice daily administration of the topical compositions, or intermittent administration of the topical compositions. Further, the period of treatment contemplated herein can be any sufficient period of time to observe a reduced incidence of rosacea, for example from about 6 to about 12 weeks, but in most cases more than 3 weeks, minimum.

Intermittent administration contemplated herein includes administration conducted other than daily (i.e. twice weekly) administration. Such intermittent administration is typically conducted when a patient commences a new treatment, as a treatment is in its final stages (i.e. as the patient is weaned off of the treatment), or as part of a maintenance regimen. Typically, intermittent administration is conducted more than once per week, but less than once per day. This intermittent treatment is especially useful when a patient starts a new treatment regimen to build their tolerance to the new medicine, and is typically followed by a more regular administration regimen.

Accordingly, it will be understood that the preferred embodiment of the present invention has been disclosed by way of example and that other modifications and alterations may occur to those skilled in the art.

I claim:

1. A topical composition for the treatment of mammalian skin dermatoses comprising at least one sulfacetamide or a salt thereof, sulfur and at least one sunscreen, wherein the sunscreen is present in a sufficient amount to produce a sun protection factor of about 1.6 to about 20.6 and is selected from the group consisting of p-aminobenzoic acid, avobenzone, cinozate, dioxybenzone, ensulizole, homosalate, methyl anthranilate, octocrylene, octyl dimethyl PABA, octyl methoxycinnamate, octyl salicylate, oxybenzone, sulisobenzone, trolamine salicylate, 3-benzylidene camphor, benzylidene camphor sulfonic acid, bisymidazylate, camphor benzalkonium methosulfate, diethylamino hydroxybenzoyl hexyl benzoate, diethylhexyl butamido triazone, diemethicodiethylbenzal malonate, drometrizole trisiloxane, ecamsule, isoamyl p-methoxycinnamate, 4-methylbenzylidene camphor, octyl triazone, PEG 25-PABA, polyacrylamidomethyl benzylidene camphor, sulisobenzone, tinosorb M, tinosorb S and mixtures thereof.

2. The composition of claim 1, wherein the sunscreen is present in a sufficient amount to produce a sun protection factor of about 8 to about 20.

3. The composition of claim 1, wherein the sunscreen is present in a sufficient amount to produce a sun protection factor of about 8 to about 15.

4. The composition of claim 1, wherein the sunscreen is present in a sufficient amount to produce a sun protection factor of about 15 to about 20.

5. The composition of claim 1 wherein the dermatoses is selected from the group consisting of topical bacterial infections, rosacea, impetigo, folliculitis, erythasma, and combinations thereof.

6. The composition of claim 1 wherein the dermatoses is selected from the group consisting of gram positive bacteria, gram negative bacteria, and a combination thereof.

7. The composition of claim 1 wherein the dermatoses is selected from the group consisting of antimicrobial resistant bacterial infections, atopic dermatitis, bromhidrosis, chronic paronychia, desquamative inflammatory vaginitis, Fox Fordyce Disease, Hailey-Hailey Disease, Hidradenitits suppurativa, intertrigo, nummular dermatitis, otopyorrhea, perioral dermatitis, angular chelitis, psoriasis, seborrheic dermatitis, skin ulcers, and combinations thereof.

8. A method of treating mammalian dermatoses by administering a topical composition comprising at least one sulfacetamide or a salt thereof, sulfur and at least one sunscreen, wherein the sunscreen is present in a sufficient amount to produce a sun protection factor of about 1.6 to about 20.6 and is selected from the group consisting of p-aminobenzoic acid, avobenzone, cinozate, dioxybenzone, ensulizole, homosalate, methyl anthranilate, octocrylene, octyl dimethyl PABA, octyl methoxycinnamate, octyl salicylate, oxybenzone, sulisobenzone, trolamine salicylate, 3-benzylidene camphor, benzylidene camphor sulfonic acid, bisymidazylate, camphor benzalkonium methosulfate, diethylamino hydroxybenzoyl hexyl benzoate, diethylhexyl butamido triazone, diemethicodiethylbenzal malonate, drometrizole trisiloxane, ecamsule, isoamyl p-methoxycinnamate, 4-methylbenzylidene camphor, octyl triazone, PEG 25-PABA, polyacrylamidomethyl benzylidene camphor, sulisobenzone, tinosorb M, tinosorb S and mixtures thereof.

9. The method of claim 8, wherein the sunscreen is present in a sufficient amount to produce a sun protection factor of about 8 to about 20.

10. The method of claim 8, wherein the sunscreen is present in a sufficient amount to produce a sun protection factor of about 8 to about 15.

11. The method of claim 8, wherein the sunscreen is present in a sufficient amount to produce a sun protection factor of about 15 to about 20.

12. The method of claim 8 wherein the dermatoses is selected from the group consisting of topical bacterial infections, rosacea, impetigo, folliculitis, erythasma, and combinations thereof.

13. The method of claim 8 wherein the dermatoses is selected from the group consisting of gram positive bacteria, gram negative bacteria, and a combination thereof.

14. The method of claim 8 wherein the dermatoses is selected from the group consisting of antimicrobial resistant bacterial infections, atopic dermatitis bromhidrosis, chronic paronychia, desquamative inflammatory vaginitis, Fox Fordyce Disease, Hailey-Hailey Disease, Hidradenitits suppurativa, intertrigo, nummular dermatitis, otopyorrhea, perioral dermatitis, angular chelitis, psoriasis, seborrheic dermatitis, skin ulcers, and combinations thereof.

15. A topical composition for the treatment of mammalian skin dermatoses comprising sulfacetamide, sulfur and at least one sunscreen, wherein the sunscreen is present in a sufficient amount to produce a sun protection factor of about 1.6 to about 20.6, the sunscreen is selected from the group consisting of p-aminobenzoic acid, avobenzone, cinozate, dioxybenzone, ensulizole, homosalate, methyl anthranilate, octocrylene, octyl dimethyl PABA, octyl methoxycinnamate, octyl salicylate, oxybenzone, sulisobenzone, trolamine salicylate, 3-benzylidene camphor, benzylidene camphor sulfonic acid, bisymidazylate, camphor benzalkonium methosulfate, diethylamino hydroxybenzoyl hexyl benzoate, diethylhexyl butamido triazone, diemethicodiethylbenzal malonate, drometrizole trisiloxane, ecamsule, isoamyl p-methoxycinnamate, 4-methylbenzylidene camphor, octyl triazone, PEG 25-PABA, polyacrylamidomethyl benzylidene camphor, sulisobenzone, tinosorb M, tinosorb S and mixtures thereof, and wherein the composition exhibits less than 10% decomposition of sulfacetamide or sunscreen after storage at 2500 for 180 days.

16. The composition of claim 15, wherein the sunscreen is present in a sufficient amount to produce a sun protection factor of about 8 to about 20.

17. The composition of claim 15, wherein the sunscreen is present in a sufficient amount to produce a sun protection factor of about 8 to about 15.

18. The composition of claim 15, wherein the sunscreen is present in a sufficient amount to produce a sun protection factor of about 15 to about 20.

19. The composition of claim 15 wherein the dermatoses is selected from the group consisting of topical bacterial infections, rosacea, impetigo, folliculitis, erythasma, and combinations thereof.

20. The composition of claim 15 wherein the dermatoses is selected from the group consisting of gram positive bacteria, gram negative bacteria, and a combination thereof.

21. The composition of claim 15 wherein the dermatoses is selected from the group consisting of antimicrobial resistant bacterial infections, atopic dermatitis, bromhidrosis, chronic paronychia, desquamative inflammatory vaginitis, Fox Fordyce Disease, Hailey-Hailey Disease, Hidradenitits suppurativa, intertrigo, nummular dermatitis, otopyorrhea, perioral dermatitis, angular chelitis, psoriasis, seborrheic dermatitis, skin ulcers, and combinations thereof.

* * * * *